United States Patent
Jin

(10) Patent No.: US 10,420,953 B2
(45) Date of Patent: Sep. 24, 2019

(54) RTMS PULSE FREQUENCY OPTIMIZATION

(71) Applicant: Kosivana Holdings Limited, Limassol (CY)

(72) Inventor: Yi Jin, Irvine, CA (US)

(73) Assignee: WAVE NEUROSCIENCE, INC., Newport Beach, CA (US)

( * ) Notice: Subject to any disclaimer, the term of this patent is extended or adjusted under 35 U.S.C. 154(b) by 289 days.

(21) Appl. No.: 15/249,358

(22) Filed: Aug. 27, 2016

(65) Prior Publication Data
US 2018/0056083 A1   Mar. 1, 2018

(51) Int. Cl.
| | |
|---|---|
| *A61N 2/00* | (2006.01) |
| *A61N 2/02* | (2006.01) |
| *A61B 5/0476* | (2006.01) |
| *A61B 5/00* | (2006.01) |
| *A61B 5/048* | (2006.01) |

(52) U.S. Cl.
CPC .............. *A61N 2/006* (2013.01); *A61B 5/048* (2013.01); *A61B 5/0476* (2013.01); *A61B 5/4836* (2013.01); *A61B 5/4848* (2013.01); *A61B 5/7257* (2013.01); *A61N 2/02* (2013.01)

(58) Field of Classification Search
CPC .............. A61N 2/00–12; A61B 5/4836; A61B 5/0036; A61B 5/0476
See application file for complete search history.

(56) References Cited

U.S. PATENT DOCUMENTS

| | | | | |
|---|---|---|---|---|
| 5,218,530 | A * | 6/1993 | Jastrzebski | A61B 5/0484 345/419 |
| 5,335,657 | A | 8/1994 | Terry, Jr. et al. | |
| 8,029,431 | B2 | 10/2011 | Tononi | |
| 8,475,354 | B2 * | 7/2013 | Phillips | A61N 2/12 600/14 |
| 8,914,119 | B2 | 12/2014 | Wu et al. | |
| 9,033,861 | B2 | 5/2015 | Fischell et al. | |
| 9,308,385 | B2 | 4/2016 | Jin | |
| 2009/0319004 | A1 * | 12/2009 | Sabel | A61H 5/00 607/54 |
| 2012/0271375 | A1 * | 10/2012 | Wu | A61N 1/36067 607/45 |
| 2013/0267760 | A1 * | 10/2013 | Jin | A61N 2/004 600/9 |
| 2016/0199662 | A1 * | 7/2016 | Wundrich | A61N 2/02 600/9 |

FOREIGN PATENT DOCUMENTS

WO    2008109508 A2    9/2008

* cited by examiner

*Primary Examiner* — Catherine B Kuhlman
(74) *Attorney, Agent, or Firm* — Saliwanchik, Lloyd & Eisenschenk

(57) ABSTRACT

Repetitive Transcranial Magnetic Stimulation (rTMS) is administered at a pulse frequency that is optimized with respect to settling time of the EEG oscillations, measured at the pulse frequency. Pulse frequency is adjusted following each pulse train to achieve a maximum settling time. A device is disclosed which is configured to allow for magnetic pulse frequency optimization.

11 Claims, 3 Drawing Sheets

RTMS PULSE FREQUENCY OPTIMIZATION

FIELD OF THE INVENTION

The present invention relates to methods and devices to modulate brain activity with repetitive transcranial magnetic stimulation (rTMS) wherein the rTMS magnetic pulse frequency is dynamically adjusted to achieve maximum settling time of EEG oscillations following each pulse train.

BACKGROUND OF THE INVENTION

Repetitive Transcranial Magnetic Stimulation (rTMS) has been used to improve symptoms of mental disorders and to improve brain function. rTMS uses high energy magnetic pulses from a magnetic field generator that is positioned close to a person's head, so that the magnetic pulses affect a desired treatment region within the brain. Traditionally, the pulses are generated at a fixed frequency for a short time duration. For example, a typical rTMS system may generate pulses at 10 Hz for a duration of 6 seconds. A series of pulses generated over a period of time is referred to as a pulse train. An rTMS treatment session may be composed of several pulse trains, with a rest period between each pulse train. A typical rest period may be 54 seconds, such that 6 seconds of rTMS pulses are generated per minute.

The brain's neural oscillations arise from synchronous and coherent electrical activity, and can be recorded using an electroencephalogram (EEG). The dominant EEG oscillation in the range of 8-13 Hz is the Intrinsic Alpha Frequency (IAF), and can vary between individuals and over time. It has been disclosed by Phillips and Jin (U.S. Pat. No. 8,475,354) that providing magnetic pulses at a frequency that matches a person's IAF can provide an added benefit to the person when compared to rTMS at an arbitrary frequency, such as 10 Hz. In addition, it has been disclosed by Jin (U.S. Pat. No. 9,308,385) that rTMS pulses at a harmonic of a non-EEG biological metric, such as heart rate, that is close to the person's IAF may also provide an added benefit. It is evident that an optimal pulse frequency exists to provide maximum benefit from rTMS for a person.

SUMMARY

Described herein are methods and devices to treat a person by optimizing the pulse frequency of repetitive transcranial magnetic stimulation (rTMS). The methods and devices described herein do not require any medication. The methods and devices described herein optimize pulse frequency by adjusting the magnetic pulse frequency to maximize the settling time of EEG oscillations, measured at the pulse frequency, following a pulse train.

The efficacy of rTMS treatment is related to the frequency of magnetic pulses delivered to the patient. To provide optimal benefit to a person, it is advantageous to find the magnetic pulse frequency that has the most significant effect on the brain of the person. When an rTMS pulse train is being used to treat the brain of a person, the pulses put the brain into a "hyper-synchronous" state, where the brain's EEG shows significant oscillations at the pulse frequency. After the pulse train, the EEG oscillations continue for a settling time, until the EEG state becomes approximately the same as it was prior to the pulse train. Modeling the brain as a resonant system, a pulse train where the pulse frequency matches the resonant frequency of the system will result in a longer settling time after the pulse train ends. By optimizing the pulse frequency so as to maximize settling time, it is possible to have the most efficacious rTMS treatment for the person.

In one aspect the subject invention provides methods of treating a person using repetitive Transcranial Magnetic Stimulation, which has a magnetic pulse frequency, comprising the following steps:
 a. setting the magnetic pulse frequency to an initial pulse frequency value;
 b. recording a baseline EEG of the person, which contains oscillations;
 c. administering a magnetic field pulse train to a head of the person;
 d. recording an EEG of the person following the magnetic field pulse train, which contains oscillations;
 e. measuring the settling time of the EEG oscillations of the person;
 f. adjusting the pulse frequency value; and
 g. proceeding back to step (b) for a number of pulse trains over a treatment session in order to achieve an approximate global or local maximum settling time.

In order to determine settling time, the energy of EEG oscillation, measured at the pulse frequency, may be tracked to determine the amount of time following a pulse train until the energy reaches a target energy value. In some embodiments of at least one aspect described above, the settling time is the time period from the end of the pulse train until the energy of EEG oscillation, which is measured at the pulse frequency, reaches a target energy value. The target energy value may be set using the initial energy of EEG oscillations, measured at the pulse frequency. In some embodiments of at least one aspect described above, the target energy value is about ten percent the initial energy of EEG oscillation, measured at the pulse frequency. The initial energy should be calculated very soon after a pulse train ends. In some embodiments of at least one aspect described above, the initial energy is the energy of EEG oscillation recorded about ten milliseconds after the end of the pulse train.

Alternatively, the target energy value may be set using the energy of the baseline EEG oscillation before the pulse train begins. In some embodiments of at least one aspect described above, the target energy value is directly proportional to the energy of baseline EEG oscillation, measured at the pulse frequency. This allows the target energy to be adjusted based on variations in the energy of EEG oscillations between individuals and over time.

The adjustment to the pulse frequency value may be done using optimization, with the pulse frequencies and settling times from all previous pulse trains as input to the optimization routine. Many optimization algorithms exist. In some embodiments of at least one aspect described above, the adjustment to the pulse frequency is determined using gradient optimization or stochastic optimization.

The initial value for pulse frequency at the start of a treatment session may be a fixed value, based on a person's EEG, or based on a pulse frequency from a previous session. In some embodiments of at least one aspect described above, the initial pulse frequency value is set to about 10 Hz. In some embodiments of at least one aspect described above, the initial pulse frequency value is set to the person's intrinsic alpha frequency (IAF). In some embodiments of at least one aspect described above, the initial pulse frequency value is set to a harmonic of a non-EEG biological metric that is closest to the person's IAF.

It is possible to treat mental disorders effectively using rTMS at an optimal pulse frequency. In some embodiments of at least one aspect described above, the treatment is provided in order to improve symptoms of Autism Spectrum Disorder, Alzheimer's disease, ADHD, schizophrenia, anxiety, depression, coma, Parkinson's disease, substance abuse, bipolar disorder, sleep disorder, eating disorder, tinnitus, traumatic brain injury, post-traumatic stress disorder, or fibromyalgia.

The treatment may also be used to improve various functions of the body. In some embodiments of at least one aspect described above, the treatment is provided in order to improve concentration, sleep, alertness, memory, blood pressure, stress, libido, speech, motor function, physical performance, cognitive function, intelligence, or weight.

In another aspect of the present invention, a device to treat a person is described comprising:
   a) a magnetic field generator having a magnetic pulse frequency;
   b) an EEG sense electrode;
   c) an EEG reference electrode; and
   d) a processor with memory;
wherein the EEG sense electrode and EEG reference electrode are configured to record an EEG of the person after each pulse train and the processor and memory are configured to calculate the energy of an EEG oscillation at a specified frequency in order to adjust the magnetic pulse frequency to maximize a settling time of EEG oscillations following each pulse train.

The magnetic field generator is required to create magnetic pulses at a pulse frequency. In some embodiments of at least one aspect described above, the magnetic field generator comprises an electrical coil or a moving permanent magnet.

The EEG sense electrode should be situated in a location in order to provide a proper EEG recording of the EEG oscillations following a pulse train. This is preferably on or near the scalp close to the treatment location in the brain. In some embodiments of at least one aspect described above, the EEG sense electrode is positioned at about the center of the treatment surface of the magnetic field generator and makes contact with the skin of the person when the magnetic field generator is positioned above a desired treatment region.

The EEG sense electrode type is variable, but it must allow proper EEG recording. In some embodiments of at least one aspect described above, the EEG sense electrode is a dry-sensor electrode, gel electrode, or saline electrode. The EEG reference electrode should be placed elsewhere on the body in order to allow for proper EEG recording between the EEG sense electrode and EEG reference electrode. In some embodiments of at least one aspect described above, the EEG reference electrode is an ear-clip electrode.

DETAILED DESCRIPTION

Figure 1:
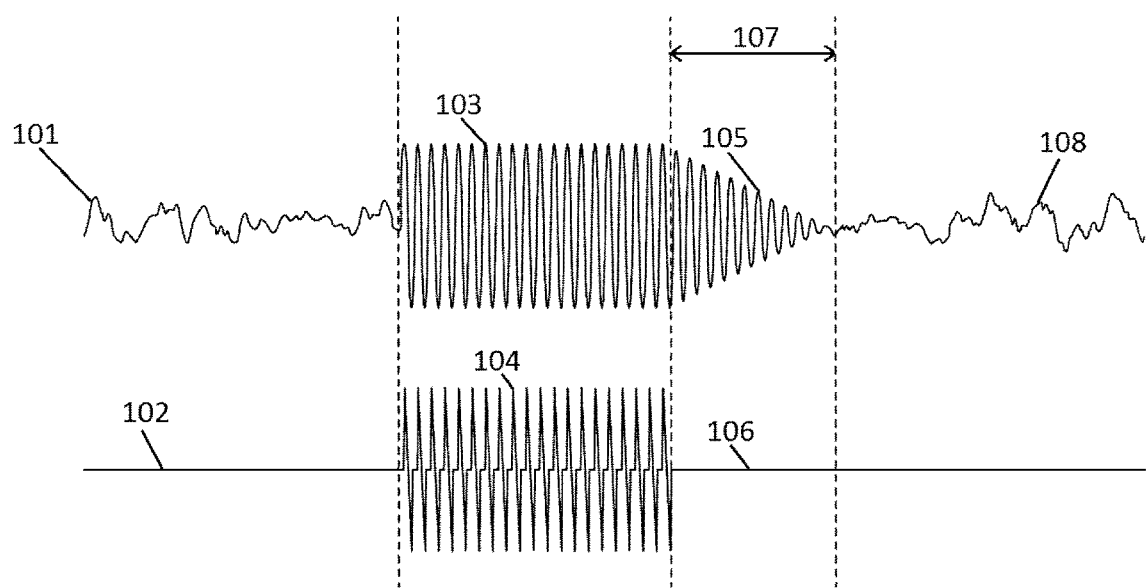
FIG. 1 shows sample EEG and magnetic field plots before, during, and after a pulse train, and includes continued EEG oscillations following the pulse train that diminish gradually over a settling time.

While certain embodiments have been provided and described herein, it will be readily apparent to those skilled in the art that such embodiments are provided by way of example only. It should be understood that various alternatives to the embodiments described herein may be employed, and are part of the invention described herein.

Described herein are methods and devices for the treatment of a person using rTMS with an optimal pulse frequency. The brain can be thought of as a resonant system, where neurons fire in a synchronous, coherent manner at a resonant frequency. If rTMS pulses are provided at or near the resonant frequency of the brain, then the effect of rTMS may be enhanced, providing additional benefit to the person.

When a stimulus is provided to a resonant system, there is a "ringing effect" when the stimulus is removed. The resonant system continues to oscillate at the resonant frequency for a period of time, gradually settling until eventually, the resonant system returns to its pre-stimulus state. An example is a bell that is struck, or a swing that is pushed at its resonant frequency and then released. The brain acts in a similar manner.

When a stimulus is provided at the brain's resonant frequency, the region of the brain being stimulated enters a "hyper-synchronous state," where neuronal firing is highly synchronous and any EEG recorded would show significant oscillations. When the stimulus is removed, the stimulated region continues to oscillate at the resonant frequency for a period of time, with oscillations gradually settling until the brain eventually returns to approximately its pre-stimulus state.

When stimulation is provided at the brain's resonant frequency, the stimulation effect is enhanced, and the ringing effect is more pronounced once the stimulation is removed, resulting in a longer time for the oscillatory behavior to settle back to pre-stimulus levels. Therefore, measuring settling time is a valid method to determine how close the stimulus frequency is to the resonant frequency of the brain. The goal of frequency optimization is to achieve an approximate global or local maximum settling time of EEG oscillations following a magnetic pulse train.

It is not necessary to perform a whole-head EEG using multiple channels, although a multiple-channel EEG would not be precluded. Instead, only a single channel EEG is necessary to record the settling time of EEG oscillations in the brain region targeted by stimulation. An EEG sense electrode may be positioned in order to record the EEG of the person in the targeted brain region. A reference electrode could be positioned elsewhere on the body to achieve the best EEG signal possible. The sense electrode could be attached to the scalp of the person, or attached to the treatment surface itself. If it is attached to the treatment surface, then it would be brought into contact with the scalp of the person each time the treatment surface is positioned to administer magnetic pulses to the brain of the person, allowing EEG recording before and after stimulation.

The term "settling time" when referring to stimulus frequency optimization, is the time after the magnetic pulse train ends until the energy of EEG oscillation, measured at the pulse frequency, has returned to about its pre-stimulus level. The term "target energy value" is a threshold for the energy of EEG oscillation, measured at the pulse frequency, that signals when settling time has ended. Since EEG oscillations tend to come in bursts, a proper target energy value may be difficult to determine. One option is to calculate an energy of the EEG oscillation, measured at the pulse frequency, very soon after stimulation ends, referred to as the "initial energy," and set the target energy value as a percentage of the initial energy. Another option is to record EEG before stimulation, referred to as the "baseline EEG", and set the target energy value as a factor of the energy of the baseline EEG oscillation, measured at the pulse frequency.

The energy of EEG oscillation may be found using the Fourier Transform of a window about a particular EEG sample. The energy at the pulse frequency is proportional to the square of the magnitude of the Fourier Transform at that frequency.

It is not necessary to use energy to calculate settling time, but any metric that is chosen should be proportional to the energy of the EEG oscillation. Some possible metrics could be the Fourier Transform magnitude, the magnitude of a sinusoid with a frequency equal to the pulse frequency convolved with the signal, the amplitude of the signal after a bandpass filter around the pulse frequency, or simply the amplitude of the signal itself.

In one aspect the subject invention provides methods of treating a person using repetitive Transcranial Magnetic Stimulation, which has a magnetic pulse frequency, comprising the following steps:
  a) setting the magnetic pulse frequency to an initial pulse frequency value;
  b) recording a baseline EEG of the person, which contains oscillations;
  c) administering a magnetic field pulse train to a head of the person;
  d) recording an EEG of the person following the magnetic field pulse train, which contains oscillations;
  e) measuring the settling time of the EEG oscillations of the person;
  f) adjusting the pulse frequency value; and
  g) proceeding back to step (b) for a number of pulse trains over a treatment session in order to achieve an approximate global or local maximum settling time.

In some embodiments of at least one aspect described above, the settling time is the time period from the end of the pulse train until the energy of EEG oscillation, which is measured at the pulse frequency, reaches a target energy value. The target energy value is set so that the settling time is proportional to the ringing effect previously described.

The target energy value may be set to a percentage of the initial energy of EEG oscillation, following a pulse train. Preferably, the target value is set to about 10% of the initial energy. However, other percentages may be used, such as 25% or 50%. In some embodiments of at least one aspect described above, the target energy value is about ten percent the initial energy of EEG oscillation, measured at the pulse frequency.

The initial energy of EEG oscillation is the energy recorded very soon after the pulse train has ended. However, it may be necessary to delay a period of time before calculating initial energy, in order to allow for transient effects of the magnetic pulse train to end. Preferably, the initial energy is the energy of EEG oscillation recorded about ten milliseconds after the end of the pulse train. However, other time periods may be required or allowed. For example, the initial energy may be the energy of EEG oscillation recorded about one millisecond, 100 milliseconds, or 1 second after the end of the pulse train. In some embodiments of at least one aspect described above, the initial energy is the energy of EEG oscillation recorded about ten milliseconds after the end of the pulse train.

Oscillatory EEG activity varies among individuals and varies over time and location as well. If a person has a large amount of natural oscillatory activity at the pulse frequency, the energy of EEG oscillation, measured at the pulse frequency, may not reach the threshold defined by the target energy following a pulse train if the target energy is lower than the natural energy of EEG oscillation. Therefore, it may be required to base the target energy on the natural energy of baseline EEG oscillation, measured at the pulse frequency, before the pulse train begins. This way, if the natural baseline EEG oscillation, measured at the pulse frequency, is high, the target energy value may be raised to accommodate for the larger natural energy of EEG oscillation. By the same token, the target energy value may be lowered if the natural baseline EEG oscillation, measured at the pulse frequency, is low. In some embodiments of at least one aspect described above, the target energy value is directly proportional to the energy of baseline EEG oscillation, measured at the pulse frequency.

The adjustment of pulse frequency after each pulse train is performed in order to maximize settling time. A number of optimization algorithms exist in order to accomplish this. In some embodiments of at least one aspect described above, the adjustment to the pulse frequency is determined using gradient optimization or stochastic optimization. Stochastic optimization uses random variables to determine adjustments. Some examples of stochastic optimization are simulated annealing, random search, stochastic tunneling, and stochastic hill climbing. Gradient optimization involves finding a local/global optimum by adjusting steps proportional to the gradient of the function (the change in settling time divided by the change in pulse frequency). In all optimization methods, the inputs comprise the settling time and pulse frequency of all previous pulse trains. The result that is achieved using an optimization algorithm will preferably result in the maximum settling time over all possible stimulation frequencies; however, the final result may not be exactly the maximum settling time. Instead, an algorithm may result in an approximate maximum, based on the algorithm method and discrete frequency adjustments. Also, it is possible for algorithms to finalize on, or near, a local maximum, instead of achieving a global maximum, due to the nonlinear nature of settling time versus stimulation frequency.

When performing frequency optimization, it is necessary to specify an initial value for the magnetic pulse frequency. This value may be fixed, based on the person's EEG, or based on a pulse frequency value used in a prior treatment session. In some embodiments of at least one aspect described above, the initial pulse frequency value is set to about 10 Hz. This value is near the center of the Alpha EEG band, which may contain the optimal stimulation frequency. However, other values may be chosen, such as 6 Hz, 8 Hz, 12 Hz, or 20 Hz. In some embodiments of at least one aspect described above, the initial pulse frequency value is set to the person's intrinsic alpha frequency (IAF).

As described previously, rTMS administered with a pulse frequency set to a person's IAF has been shown to be efficacious in the treatment of mental disorders, and it would be a natural choice for an estimate of the resonant frequency of the brain. In some embodiments of at least one aspect described above, the initial pulse frequency value is set to a harmonic of a non-EEG biological metric that is closest to the person's IAF. Evidence has shown that rTMS administered at this frequency is also effective at treating mental disorders.

In some embodiments of at least one aspect described above, the initial pulse frequency value is set to the final pulse frequency value from a previous treatment session of the person. This would be a reasonable estimate, since the optimal frequency is not expected to change appreciably from one session to the next.

rTMS at or near the optimal pulse frequency may be used to treat a number of mental disorders. In some embodiments of at least one aspect described above, the treatment is provided in order to improve symptoms of Autism Spectrum Disorder, Alzheimer's disease, ADHD, schizophrenia, anxiety, depression, coma, Parkinson's disease, substance abuse, bipolar disorder, sleep disorder, eating disorder, tinnitus, traumatic brain injury, post-traumatic stress disorder, or fibromyalgia.

The treatment may also be used to improve various functions of the body. In some embodiments of at least one aspect described above, the treatment is provided in order to improve concentration, sleep, alertness, memory, blood pressure, stress, libido, speech, motor function, physical performance, cognitive function, intelligence, or weight.

In another aspect of the present invention, a device to treat a person is described comprising:
a) a magnetic field generator having a magnetic pulse frequency;
b) an EEG sense electrode;
c) an EEG reference electrode; and
d) a processor with memory;
wherein the EEG sense electrode and EEG reference electrode are configured to record an EEG of the person after each pulse train and the processor and memory are configured to calculate the energy of an EEG oscillation at a specified frequency in order to adjust the magnetic pulse frequency to maximize a settling time of EEG oscillations following each pulse train.

Preferably, the magnetic field generator comprises an electrical coil that generates magnetic pulses using induction. However, the magnetic pulses could also be generated by moving a permanent magnet. For example, a permanent magnet could be moved linearly, rotationally, or in a swaying motion to create magnetic field pulses that affect the treatment region in the brain. In some embodiments of at least one aspect described above, the magnetic field generator comprises an electrical coil or a moving permanent magnet.

The sense EEG electrode is configured to record the EEG oscillations of the person in order to determine settling time following a pulse train. Due to entrainment in the brain and the distributed nature of EEG activity, the electrode could be located anywhere on the scalp nearby the treatment location. However, preferably the electrode would be located on the scalp at or very near the treatment location in the brain. Since this is the case, the electrode could be attached to the treatment surface of the magnetic field generator, so that it is brought into close proximity with the scalp before, during, and after the pulse train is generated.

In some embodiments of at least one aspect described above, the EEG sense electrode is positioned at about the center of the treatment surface of the magnetic field generator and makes contact with the skin of the person when the magnetic field generator is positioned above a desired treatment region.

The EEG sense electrode needs to be of a type that will allow proper recording of the person's EEG. In some embodiments of at least one aspect described above, the EEG sense electrode is a dry-sensor electrode, gel electrode, or saline electrode. If the EEG sense electrode is attached to the treatment surface, it is preferable that it be a dry-sensor electrode, such as a capacitive type electrode, because the gel is likely to spread and become less effective at reducing impedance over time, as the treatment surface is repeatedly applied to the person's head throughout a treatment session.

The EEG reference electrode should be placed elsewhere on the body in order to allow for proper EEG recording through the EEG sense electrode. In some embodiments of at least one aspect described above, the EEG reference electrode is an ear-clip electrode.

FIG. 1 shows an example plot of the EEG of a person and the magnitude of the magnetic field generated by the magnetic field generator. The EEG before the magnetic pulse train (101) shows normal random activity, without significant oscillatory behavior. There is no magnetic field being generated (102). During the magnetic pulse train generation (104), the EEG becomes "hyper-synchronous" (103), being driven by the powerful magnetic pulses at the pulse frequency. This lasts for the duration of the pulse train. Once the pulse train ends (106), the EEG continues its oscillatory behavior for a period of time (105), where the energy of EEG oscillations, measured at the pulse frequency, settles out over time, until after the settling time (107), the EEG returns to a state similar to before the EEG pulse train (108). Although this example shows a fairly linear decrease in the energy of EEG oscillations, measured at the pulse frequency, the energy may decrease nonlinearly. For example, the energy decrease may be exponential or may vary significantly as it moves toward the target energy.

Figure 2:
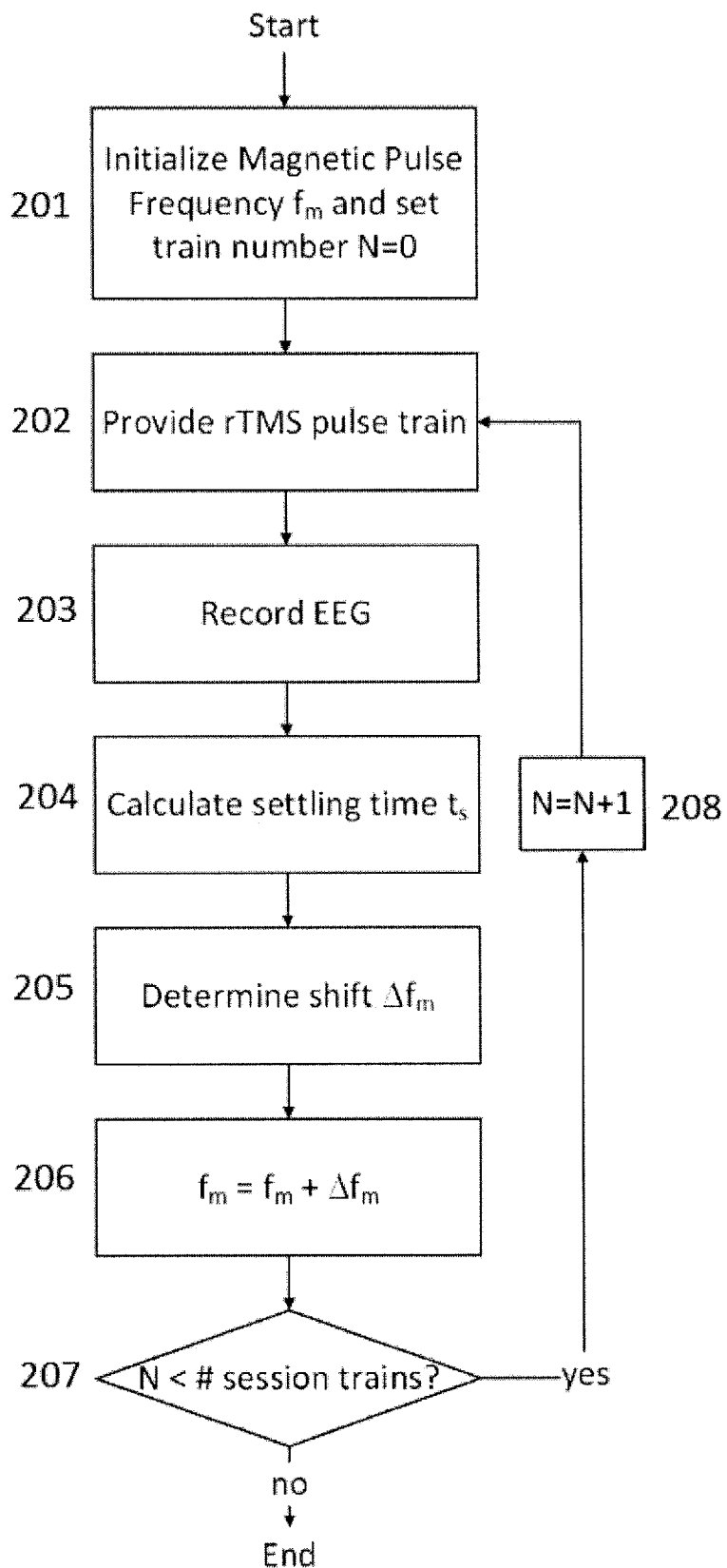
FIG. 2 shows a sample flowchart of the method of optimizing the pulse frequency during a treatment session based on settling time of the energy of EEG oscillations, measured at the pulse frequency.

FIG. 2 shows an example flowchart of the frequency optimization method. The magnetic pulse frequency $f_m$ is initialized to a particular value, with the train number N set to 0 (201). A pulse train is generated at the magnetic pulse frequency (202). Afterward, the EEG of the patient is recorded between the EEG sense electrode and the EEG reference electrode (203). The settling time $t_s$ is calculated by determining when the energy of EEG oscillation, measured at the pulse frequency, drops below the target energy (204). From this, an optimization routine is used to determine a shift to the magnetic pulse frequency $\Delta f_m$, based on the previous settling times and pulse frequency values during the session (205). The pulse frequency value is updated (206), and the train number N is checked to see if it is less than the number of trains in the current session (207). If so, then N is incremented (208) and the next pulse train is delivered. Otherwise, the algorithm ends.

Figure 3:
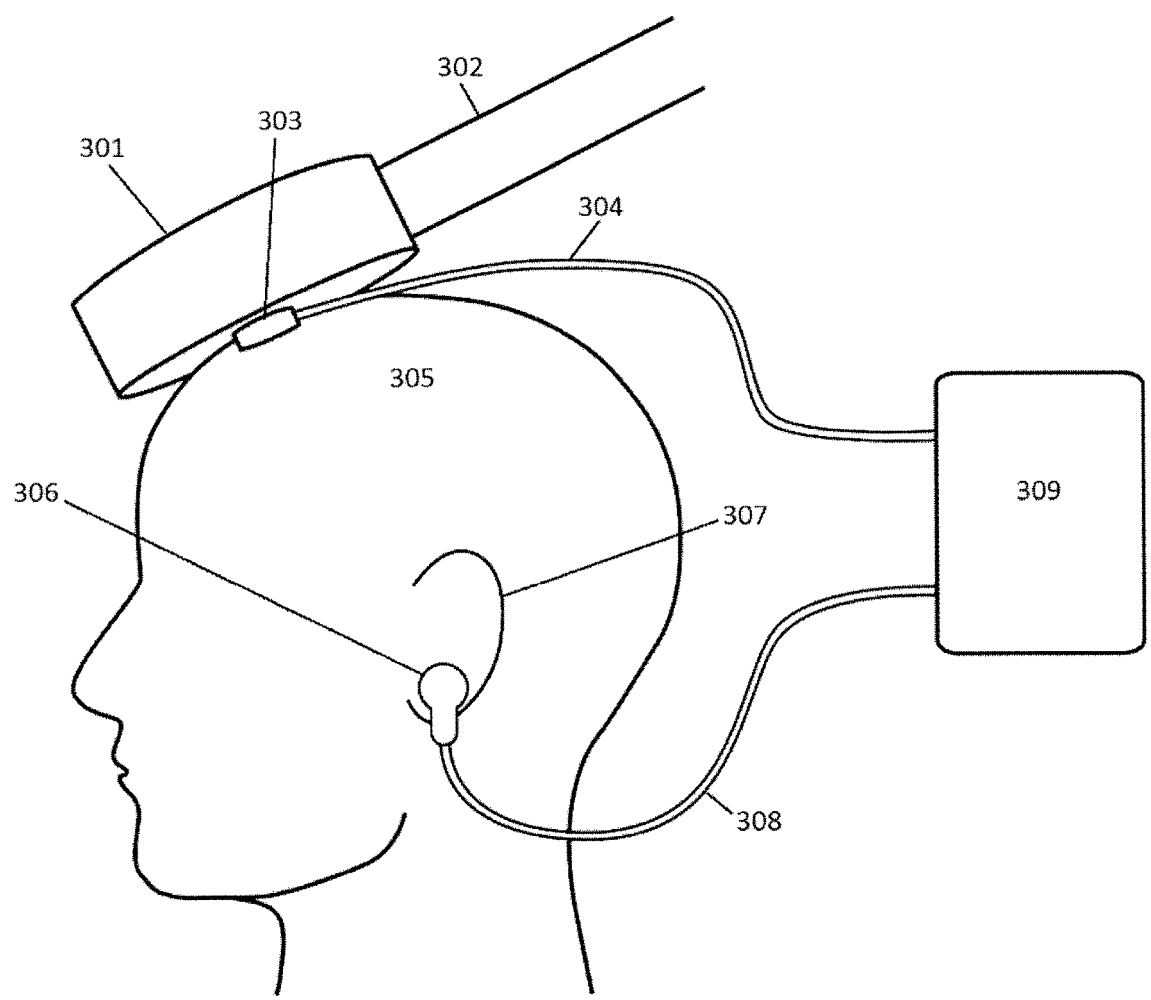
FIG. 3 shows an exemplary device with the EEG sense electrode positioned on the treatment surface of a coil-type magnetic field generator.

FIG. 3 shows an exemplary device in which a coil (301) and handle (302) are positioned so that magnetic pulses are generated near the head (305) of a person. An EEG sense electrode (303) is attached to the coil treatment surface so that it comes in close proximity to the scalp of the person when the coil is positioned to administer magnetic pulses to the brain of the person. The EEG sense electrode is connected via a lead wire (304) to an EEG amplifier, processor and memory (309) to allow for EEG recording following a pulse train and adjustment of the pulse frequency. The EEG reference electrode (306) is clipped to the ear of the person (307), and connected via its lead wire (308) to the EEG amplifier and processor (309).

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word:

any of the items in the list, all of the items in the list and any combination of the items in the list.

The above descriptions of illustrated embodiments of the methods or devices are not intended to be exhaustive or to be limited to the precise form disclosed. While specific embodiments of, and examples for, the methods or devices are described herein for illustrative purposes, various equivalent modifications are possible within the scope of the methods or devices, as those skilled in the relevant art will recognize. The teachings of the methods, or devices provided herein can be applied to other processing methods or devices, not only for the methods or devices described.

The elements and acts of the various embodiments described can be combined to provide further embodiments. These and other changes can be made to the device in light of the above detailed description.

In general, in the following claims, the terms used should not be construed to limit the methods or devices to the specific embodiments disclosed in the specification and the claims, but should be construed to include all processing devices that operate under the claims. Accordingly, the methods and devices are not limited by the disclosure, but instead the scopes of the methods or devices are to be determined entirely by the claims.

While certain aspects of the methods or devices are presented below in certain claim forms, the inventor contemplates the various aspects of the methods or devices in any number of claim forms. Accordingly, the inventors reserve the right to add additional claims after filing the application to pursue such additional claim forms for other aspects of the methods or devices.

Embodiments

Specific embodiments of the invention include the following:
1. A method of treating a person using repetitive Transcranial Magnetic Stimulation, which has a magnetic pulse frequency, comprising the following steps:
   a. setting the magnetic pulse frequency to an initial pulse frequency value;
   b. recording a baseline EEG of the person, which contains oscillations;
   c. administering a magnetic field pulse train to a head of the person;
   d. recording an EEG of the person following the magnetic field pulse train, which contains oscillations;
   e. measuring the settling time of the EEG oscillations of the person; and
   f. adjusting the pulse frequency value; and
   g. proceeding back to step (b) for a number of pulse trains over a treatment session in order to achieve an approximate global or local maximum settling time.
2. The method of Embodiment 1 wherein the settling time is the time period from the end of the pulse train until the energy of the EEG oscillation, which is measured at the pulse frequency, reaches a target energy value.
3. The method of Embodiment 2 wherein the target energy value is about ten percent the initial energy of EEG oscillation, measured at the pulse frequency.
4. The method of Embodiment 3 wherein the initial energy is the energy of EEG oscillation recorded about ten milliseconds after the end of the pulse train.
5. The method of Embodiment 2 wherein the target energy value is directly proportional to the energy of the baseline EEG oscillation, measured at the pulse frequency.
6. The method of Embodiment 1 wherein the adjustment to the pulse frequency is determined using gradient optimization or stochastic optimization.
7. The method of Embodiment 1 wherein the initial pulse frequency value is set to about 10 Hz.
8. The method of Embodiment 1 wherein the initial pulse frequency value is set to the person's intrinsic alpha frequency.
9. The method of Embodiment 1 wherein the initial pulse frequency value is set to a harmonic of a non-EEG biological metric that is closest to the person's intrinsic alpha frequency.
10. The method of Embodiment 1 wherein the initial pulse frequency value is set to the final pulse frequency value from a previous treatment session of the person.
11. The method of Embodiment 1 wherein the treatment is provided in order to improve symptoms of Autism Spectrum Disorder, Alzheimer's disease, ADHD, schizophrenia, anxiety, depression, coma, Parkinson's disease, substance abuse, bipolar disorder, sleep disorder, eating disorder, tinnitus, traumatic brain injury, post-traumatic stress disorder, or fibromyalgia.
12. The method of Embodiment 1 wherein the treatment is provided in order to improve concentration, sleep, alertness, memory, blood pressure, stress, libido, speech, motor function, physical performance, cognitive function, intelligence, or weight.
13. A device for providing treatment to a person comprising:
   a. an magnetic field generator having a magnetic pulse frequency;
   b. an EEG sense electrode;
   c. an EEG reference electrode; and
   d. a processor with memory
wherein the EEG sense electrode and EEG reference electrode are configured to record an EEG of the person after each pulse train and the processor and memory are configured to calculate the energy of an EEG oscillation at a specified frequency in order to adjust the magnetic pulse frequency to maximize a settling time of EEG oscillations following each pulse train.
14. The device of Embodiment 13 wherein the magnetic field generator comprises an electrical coil or a moving permanent magnet.
15. The device of Embodiment 13 wherein the EEG sense electrode is positioned at about the center of the treatment surface of the magnetic field generator and makes contact with the skin of the person when the magnetic field generator is positioned above a desired treatment region.
16. The device of Embodiment 13 wherein the EEG sense electrode is a dry-sensor electrode, gel electrode, or saline electrode.
17. The device of Embodiment 13 wherein the EEG reference electrode is an ear-clip electrode.
18. The device of Embodiment 13 wherein the treatment is provided in order to improve symptoms of Autism Spectrum Disorder, Alzheimer's disease, ADHD, schizophrenia, anxiety, depression, coma, Parkinson's disease, substance abuse, bipolar disorder, sleep disorder, eating disorder, tinnitus, traumatic brain injury, post-traumatic stress disorder, or fibromyalgia.

19. The device of Embodiment 13 wherein the treatment is provided in order to improve concentration, sleep, alertness, memory, blood pressure, stress, libido, speech, motor function, physical performance, cognitive function, intelligence, or weight.

I claim:

1. A method of treating a person using repetitive Transcranial Magnetic Stimulation, which has a magnetic pulse frequency, comprising the following steps:
   a. setting the magnetic pulse frequency to an initial magnetic pulse frequency value;
   b. recording a baseline EEG of the person, which contains oscillations;
   c. administering a magnetic field pulse train to a head of the person;
   d. recording an EEG of the person following the magnetic field pulse train, which contains oscillations;
   e. measuring the settling time of the EEG oscillations of the person following administration of the magnetic field pulse train to the head of the person;
   f. adjusting the magnetic pulse frequency value using a gradient optimization technique; and
   g. proceeding back to step (b) for a number of magnetic field pulse trains over a treatment session in order to achieve a local maximum settling time.

2. The method of claim 1 wherein the settling time is the time period from the end of the administered magnetic field pulse train until an energy value of an EEG oscillation of the EEG oscillations of the person reduces to a target energy value.

3. The method of claim 2 wherein the target energy value is about ten percent of an initial energy value of an EEG oscillation after administration of the magnetic field pulse train.

4. The method of claim 3 wherein the initial energy value is a value of an energy of an EEG oscillation recorded about ten milliseconds after the end of the magnetic field pulse train.

5. The method of claim 2 wherein the target energy value is directly proportional to an energy of an oscillation of the recorded baseline EEG.

6. The method of claim 1 wherein the initial magnetic pulse frequency value is set to about 10 Hz.

7. The method of claim 1 wherein the initial magnetic pulse frequency value is set to the person's intrinsic alpha frequency.

8. The method of claim 1 wherein the initial magnetic pulse frequency value is set to a harmonic of a non-EEG biological metric that is closest to the person's intrinsic alpha frequency.

9. The method of claim 1 wherein the initial magnetic field pulse frequency value is set to a final magnetic pulse frequency value from a previous treatment session of the person.

10. The method of claim 1 wherein the treatment is provided in order to improve symptoms of Autism Spectrum Disorder, Alzheimer's disease, ADHD, schizophrenia, anxiety, depression, coma, Parkinson's disease, substance abuse, bipolar disorder, sleep disorder, eating disorder, tinnitus, traumatic brain injury, post-traumatic stress disorder, or fibromyalgia.

11. The method of claim 1 wherein the treatment is provided in order to improve concentration, sleep, alertness, memory, blood pressure, stress, libido, speech, motor function, physical performance, cognitive function, intelligence, or weight.

* * * * *